United States Patent
Maale

(10) Patent No.: US 11,426,284 B2
(45) Date of Patent: Aug. 30, 2022

(54) MODULAR ROTATIONAL DEVICE FOR TORSIONALLY STABILIZING AN ENDOPROSTHESIS

(71) Applicant: Gerhard E. Maale, Plano, TX (US)

(72) Inventor: Gerhard E. Maale, Plano, TX (US)

( * ) Notice: Subject to any disclaimer, the term of this patent is extended or adjusted under 35 U.S.C. 154(b) by 75 days.

(21) Appl. No.: 15/808,111

(22) Filed: Nov. 9, 2017

(65) Prior Publication Data
US 2018/0064548 A1  Mar. 8, 2018
US 2020/0297500 A9  Sep. 24, 2020

Related U.S. Application Data

(63) Continuation of application No. 15/171,131, filed on Jun. 2, 2016, now Pat. No. 10,485,669, which is a (Continued)

(51) Int. Cl.
*A61F 2/40* (2006.01)
*A61F 2/36* (2006.01)
(Continued)

(52) U.S. Cl.
CPC .............. *A61F 2/4059* (2013.01); *A61F 2/28* (2013.01); *A61F 2/3607* (2013.01);
(Continued)

(58) Field of Classification Search
CPC .. A61F 2002/30364; A61F 2002/30365; A61F 2002/30375; A61F 2002/30639;
(Continued)

(56) References Cited

U.S. PATENT DOCUMENTS 4,225,981 A * 10/1980 Zeibig ................... A61F 2/3609
29/447
4,776,851 A  10/1988 Bruchman et al.
(Continued)

FOREIGN PATENT DOCUMENTS

DE  19931670 C1  2/2001
DE  199 31 882 C1 * 5/2001 ............... A61F 2/30
(Continued)

OTHER PUBLICATIONS

Computer generated translation of DE 19921670 C1, published Feb. 15, 2001.
(Continued)

*Primary Examiner* — David H Willse
(74) *Attorney, Agent, or Firm* — Steven H. Washam; Washam PLLC

(57) ABSTRACT

An improved modular rotational device includes a first and second threaded coupler for affixation along the stem of an endoprosthetic device, for example, a humeral prosthesis or a femoral prosthesis. The rotational device axis of rotation is coaxial with the stem, and its axis of rotation is located in close proximity to the intramedullary stem of the prosthesis or in close proximity to the distal articulation of the prosthesis. A housing has a proximal and distal end with an axial bore therethrough for receiving an elongated stem of the device. A lobe ring may be utilized to limit the axis of rotation of the device. Additional endoprosthetic devices may be attached to male or female threaded couplers, or to Morse tapers. A plurality of suture attachments facilitates attachment of soft tissue thereto.

20 Claims, 9 Drawing Sheets

Related U.S. Application Data continuation of application No. 14/680,897, filed on Apr. 7, 2015, now abandoned.

(51) Int. Cl.
    *A61F 2/38* (2006.01)
    *A61F 2/28* (2006.01)
    *A61F 2/30* (2006.01)
    *A61F 2/08* (2006.01)

(52) U.S. Cl.
    CPC ............ *A61F 2/3804* (2013.01); *A61F 2/384* (2013.01); *A61F 2/40* (2013.01); A61F 2002/0817 (2013.01); A61F 2002/0823 (2013.01); A61F 2002/2853 (2013.01); A61F 2002/30011 (2013.01); A61F 2002/30028 (2013.01); A61F 2002/30331 (2013.01); A61F 2002/30332 (2013.01); A61F 2002/30364 (2013.01); A61F 2002/30365 (2013.01); A61F 2002/30375 (2013.01); A61F 2002/30405 (2013.01); A61F 2002/30433 (2013.01); A61F 2002/30461 (2013.01); A61F 2002/30604 (2013.01); A61F 2002/30607 (2013.01); A61F 2002/30688 (2013.01); A61F 2002/30909 (2013.01); A61F 2002/368 (2013.01); A61F 2002/3822 (2013.01); A61F 2002/3827 (2013.01); A61F 2002/4011 (2013.01); A61F 2002/4018 (2013.01); A61F 2002/4085 (2013.01); A61F 2220/0008 (2013.01); A61F 2310/00011 (2013.01)

(58) Field of Classification Search
    CPC .. A61F 2002/30362; A61F 2002/30411; A61F 2002/30474; A61F 2002/30518; A61F 2002/30607
    See application file for complete search history.

(56) References Cited

U.S. PATENT DOCUMENTS

| | | | |
|---|---|---|---|
| 5,489,309 | A | 2/1996 | Lackey et al. |
| 5,549,687 | A | 8/1996 | Coates et al. |
| 6,451,061 | B1 * | 9/2002 | Grunei ............... A61F 2/60 623/40 |
| 6,663,670 | B2 | 12/2003 | Rogers et al. |
| 6,676,704 | B1 | 1/2004 | Pope et al. |
| 6,740,124 | B1 * | 5/2004 | Laghi ............... A61F 2/60 623/27 |
| 6,827,343 | B2 | 12/2004 | Skiera |
| 6,955,692 | B2 * | 10/2005 | Grundei ............... A61F 2/60 623/40 |
| 7,175,664 | B1 | 2/2007 | Lakin |
| 7,297,163 | B2 | 11/2007 | Huebner |
| 7,435,263 | B2 | 10/2008 | Barnett et al. |
| 7,998,218 | B1 | 8/2011 | Brown |
| 8,292,895 | B2 | 10/2012 | Bubb |
| 8,343,226 | B2 | 1/2013 | Nogarin et al. |
| 8,986,398 | B2 | 3/2015 | Poulson et al. |
| 2003/0139818 | A1 | 7/2003 | Rogers et al. |
| 2005/0071014 | A1 | 3/2005 | Barnett et al. |
| 2009/0319055 | A1 | 12/2009 | Iversen et al. |
| 2011/0054624 | A1 | 3/2011 | Iannotti |
| 2011/0245929 | A1 | 10/2011 | Rakin et al. |
| 2012/0035733 | A1 | 2/2012 | Porter et al. |
| 2013/0090737 | A1 | 4/2013 | Flaherty et al. |
| 2013/0150977 | A1 | 6/2013 | Gabriel et al. |
| 2013/0204390 | A1 | 8/2013 | Podolsky |
| 2014/0025173 | A1 | 1/2014 | Cardon et al. |

FOREIGN PATENT DOCUMENTS

| | | | | |
|---|---|---|---|---|
| DE | 10 2011 085 135 A1 * | 4/2013 | ............... | A61F 2/38 |
| EP | 0 768 066 A2 * | 4/1997 | ............... | A61F 2/36 |
| SU | 1532025 A1 | 12/1989 | | |
| WO | 2005087142 A2 | 9/2005 | | |
| WO | 2012051552 A2 | 4/2012 | | |
| WO | WO 2012/051552 A2 * | 4/2012 | ............... | A61F 2/40 |

OTHER PUBLICATIONS

Derwent Abstract of DE 199 31 670 C1 Reference to Grundei, et al. (Jul. 8, 1999); Thomson Reuters; 2016.
Derwent Abstract of SU 1532025A Reference to Akhmedov, et al. (Jan. 28, 1998); Thomson Reuters; 2017.
ISA International Search Report, PCT/US2016/025372, dated Jun. 24, 2016.
ISA, Search History, PCT/US2016/025372, dated Jun. 24, 2016.
ISA, Written Opinion, PCT/US2016/025372, dated Jun. 24, 2016.
R. Newsham-West, H. Nicholson, M. Walton, and P. Milburn; Long-term morphology of a healing bone-tendon interface: a histological observation in the sheep model; Journal of Anatomy; 2007; pp. 318-327; vol. 210; Anatomical Society of Great Britain and Ireland; Blackwell Publishing Ltd.; John Wiley & Sons; USA.
Zimmer; Anatomical Shoulder System; Zimmer Inc.; www.zimmer.com; 2010; USA.
European Patent Office; Supplementary European Search Report; EP 16 77 7080, dated Feb. 25, 2020.
EPO Communication; Extended European Search Report; dated Jan. 25, 2021; EPO.
EPO Espacenet English Translation—DE19931670 (01)—Obtained Apr. 27, 2021.
EPO Espacenet English Translation—EP0768066 (A2); Obtained Apr. 27, 2021.
EPO Extended European Search Report; Application No. 20195832.9; dated Dec. 16, 2020.

* cited by examiner

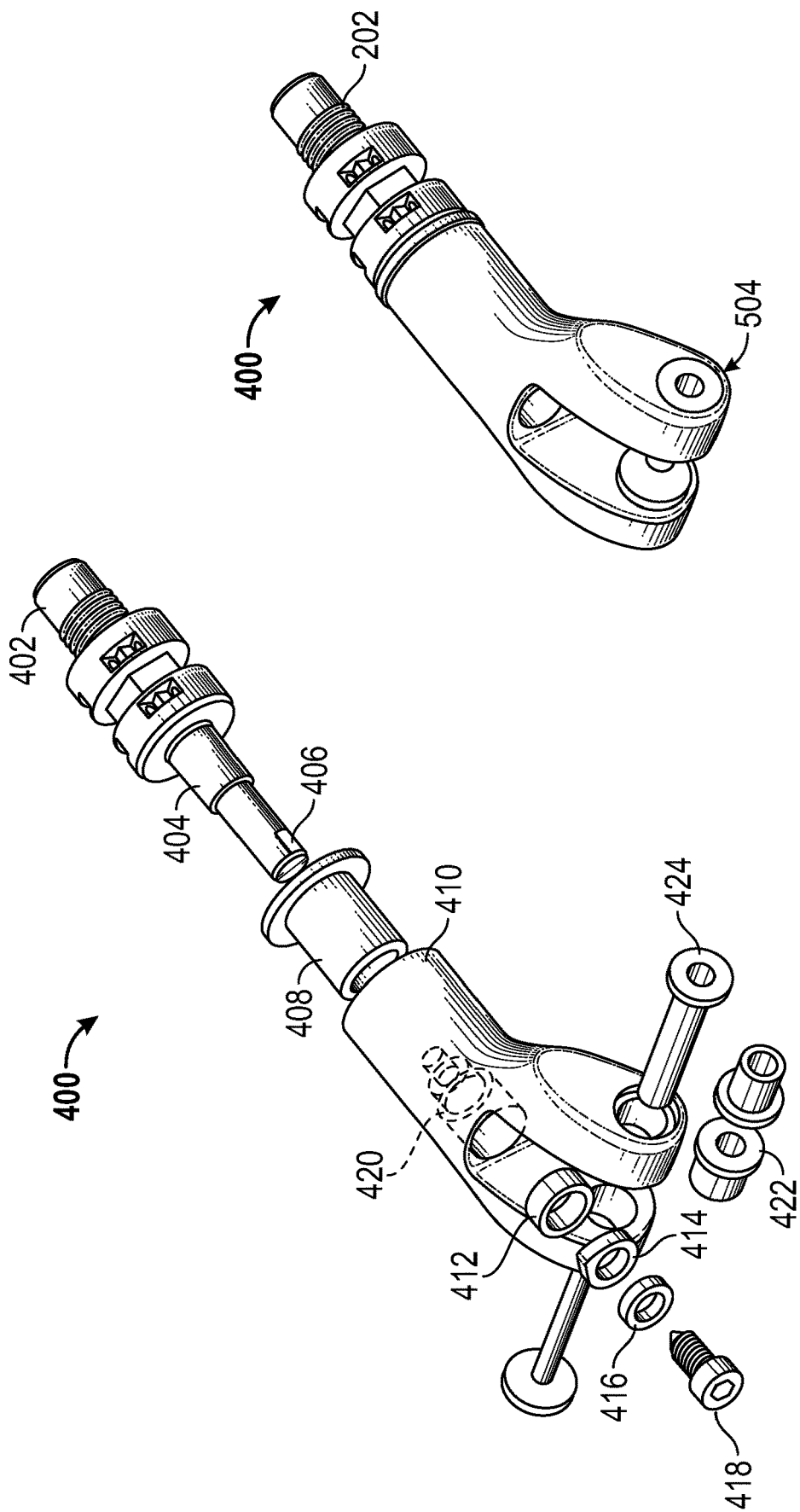

MODULAR ROTATIONAL DEVICE FOR TORSIONALLY STABILIZING AN ENDOPROSTHESIS

CROSS-REFERENCE TO RELATED APPLICATIONS

This application is a continuation of U.S. patent application Ser. No. 15/171,131, filed on Jun. 2, 2016, now U.S. Pat. No. 10,485,669, which is a continuation of U.S. patent application Ser. No. 14/680,897, filed on Apr. 7, 2015, now abandoned.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to orthopedic implant technology and, more specifically, to endoprosthetic devices for repairing segmental skeletal defects of the arm and shoulder or leg and hip of a human patient.

Description of Related Art Including Information Disclosed Under 37 CFR 1.97 and 1.98

In human patients, disease or extreme trauma can sometimes necessitate the repair or replacement of a portion or all of the bones and/or joints that comprise a patient's arm or leg. For example, a tumor that affects the proximal portion of a patient's humerus can require resection of the diseased portion and fixation of a humeral prosthesis that attempts to duplicate the functionality of the original humerus. Such an endoprosthetic device may typically include the humeral head, shaft, and even the elbow joint, with affixation at the distal end via a shaft feature that is cemented into a borehole formed within the remaining ulna or radial bone of the patient. While such extreme limb-salvage surgical repairs are made nowadays on a somewhat routine basis, existing prosthetic device technology falls short with regard to duplication of the range of movement of the original joints. Consequently, patients are typically left with limited functionality of the replaced anatomy due to limited range of motion. Moreover, patients with such repairs, who attempt arm movements to the limits of these prosthetic devices often weaken or damage the affixation site and may even cause dislocation of the shoulder joint, resulting in additional trauma to the bone and surrounding soft tissue.

The instant inventor made tremendous advances in orthopedic implant technology with his invention disclosed in PCT Application No. PCT/US2011/056393 entitled "Modular Humeral Prosthesis With Spherocentric Feature," filed on Oct. 14, 2011, the disclosure of which is incorporated by reference herein for all purposes. As the title states, this invention discloses a modular humeral prosthesis having a new and unique spherocentric elbow joint that allows full supination and pronation of the patient's hand post-recovery. However, as with this and other current humeral prostheses it was discovered that upon repeated medial and lateral rotation of the patient's repaired arm excessive torsional stresses were imparted on the humeral prosthesis shaft. In the case of complete shoulder repairs the excessive torsional stresses resulted in full separation and dislocation of the shoulder joint with resultant damage to the joint and surrounding soft tissue. In the case of partial humerus repair the excessive torsional stresses resulted in "windshield wiper" loosening of the cemented stem from the fixation site.

Existing humeral and femoral prosthesis are ineffective in addressing these realized shortcomings because of the fixed nature of their design. Specifically, existing designs that incorporate a rudimentary bearing or other rotational feature to allow the prosthesis head member to rotate to some degree with respect to the shaft member are limited in use and inflexible in location of the rotational feature with respect to the repaired joint. For example, specific humeral or femoral repairs require precise positioning of the rotational device aspect to improve stability and reliability of the repair. In the instance in which a humerus is undergoing repair to replace a damaged glenoid, it is beneficial to joint stability to position the rotational device as near the affixation site of the repair as practicable to reduce the rotational torque experienced by the intramedullary stem of the prosthetic. The instant invention presents such a positionable rotational device to address these and other shortcomings as will be understood by one of ordinary skill following a thorough study of the embodiments described herein.

BRIEF SUMMARY OF THE INVENTION

The present invention in a first embodiment is drawn to a modular rotational device for torsionally stabilizing an endoprosthetic device, the device comprising: a first threaded coupler including an elongated stem extending therefrom; a housing having a proximal end and a distal end with an axial bore therethrough; a proximal sleeve positioned within the housing proximal end axial bore, the proximal sleeve having an axial bore therethrough for receiving the elongated stem, the proximal sleeve reducing the rotational friction of the elongated stem with respect to the housing proximal end; a distal sleeve positioned within the housing distal end axial bore, the distal sleeve having an axial bore therethrough for receiving the elongated stem; the distal sleeve reducing the rotational friction of the elongated stem with respect to the housing distal end; a distal fastener for positively engaging the elongated stem within a distal end cavity to retain the stem within the housing distal end; and a second threaded coupler, the first threaded coupler and the second threaded coupler for attachment of an additional endoprosthetic device thereto.

Another embodiment of the device comprises a lobe ring affixed to the elongated stem for limiting the degree of the rotation of the elongated stem within the housing. Another embodiment of the device comprises a lobe ring affixed to the elongated stem, the lobe ring including a ramp feature for gradually arresting the relative joint rotation. Another embodiment of the device comprises a lobe ring affixed to the elongated stem and a rotational stop within a distal end cavity for engaging a feature on the lobe ring for limiting the degree of the rotation of the elongated stem within the housing. Another embodiment of the device comprises a distal end cavity including threads for attachment of an additional endoprosthetic device thereto. Another embodiment of the device comprises at least one Morse taper for affixation of an additional endoprosthetic device thereto. Another embodiment of the device comprises a porous mesh metal surface treatment for soft tissue growth attachment thereto. Another embodiment of the device comprises a plurality of through hole suture attachments for suture attachment of soft tissue thereto. Another embodiment of the device comprises at least one hex feature for engagement of a gripping tool therewith. Another embodiment of the device comprises a hex feature separating the housing proximal end from the housing distal end, the hex member for engagement of a gripping tool therewith.

The present invention in another embodiment is also drawn to a modular rotational device for torsionally stabilizing an endoprosthetic device, the device comprising: a first threaded coupler including an elongated stem extending therefrom; a housing having a proximal end and a distal end with an axial bore therethrough; and the distal end housing including a second threaded coupler, the first threaded coupler and the second threaded coupler for attachment of an additional endoprosthetic device thereto, the first threaded coupler adapted to rotate with respect to the second threaded coupler.

Another embodiment of the device comprises a proximal sleeve positioned within the housing proximal end axial bore, the proximal sleeve having an axial bore therethrough for receiving the elongated stem, the proximal sleeve reducing the rotational friction of the elongated stem with respect to the housing proximal end. Another embodiment of the device comprises a distal sleeve positioned within the housing distal end axial bore, the distal sleeve having an axial bore therethrough for receiving the elongated stem; the distal sleeve reducing the rotational friction of the elongated stem with respect to the housing distal end; and a distal fastener for positively engaging the elongated stem within a distal end cavity to retain the stem within the housing distal end. Another embodiment of the device comprises a lobe ring affixed to the elongated stem for limiting the degree of the rotation of the elongated stem within the housing. Another embodiment of the device comprises a distal end cavity including threads for attachment of an additional endoprosthetic device thereto. Another embodiment of the device comprises at least one Morse taper for affixation of an additional endoprosthetic device thereto. Another embodiment of the device comprises a porous mesh metal surface treatment for soft tissue growth attachment thereto. Another embodiment of the device comprises a plurality of through hole suture attachments for suture attachment of soft tissue thereto. Another embodiment of the device comprises at least one hex feature for engagement of a gripping tool therewith. Another embodiment of the device comprises a hex feature separating the housing proximal end from the housing distal end, the hex member for engagement of a gripping tool therewith.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein:

FIG. 4 is an exploded perspective view of an embodiment of a modular humeral prosthesis lower extremity device incorporating an embodiment of the rotational device;

FIG. 5 is an assembled perspective view of the embodiment;

Figure 1:
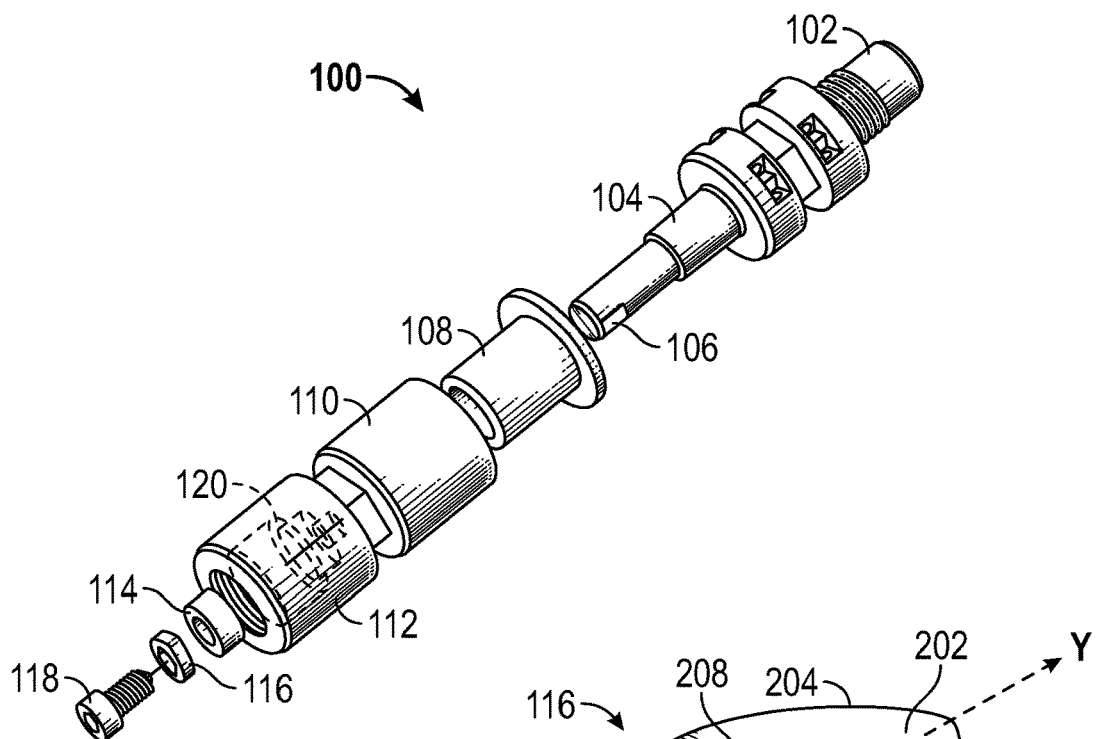
FIG. 1 is an exploded perspective view of a first embodiment of a modular rotational device of the present invention.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

The following invention makes reference to the glenohumeral articulation (shoulder joint), the humeroulnar/humeroradial articulation (elbow joint), the acetabulofemoral articulation (hip joint), and the tibiofemoral/patellofemoral articulation (knee joint) of a patient. With regard to a humerus, the proximal articulation refers to the glenohumeral articulation and the respective distal articulation refers to the humeroulnar/humeroradial articulation. With regard to a femur, the proximal articulation refers to the acetabulofemoral articulation and the respective distal articulation refers to the tibiofemoral/patellofemoral articulation.

FIG. 1 presents an exploded perspective view of a first embodiment of a modular rotational device as described herein and as utilized in the accompanying claims. As depicted, the modular rotational device (100) in this embodiment includes a machined axial component having a male threaded coupler feature (102) that is part of an elongated stem feature (104). The stem feature (104) centers the axial component within a mating passage of a machined housing component at a proximal end (110).

The housing component proximal end (110) features a through-hole axial bore within which a proximal sleeve (108) is located. The proximal sleeve (108) in this embodiment utilizes ultra-high molecular weight polyethylene (UHMWPE), but may be made from any other friction-reducing biocompatible polymer. The proximal sleeve (108), likewise, has a through-hole axial bore within which the stem feature (104) is positioned. A lip on the proximal sleeve (108) prevents the assembled axial component from directly contacting the housing component (110), thereby reducing rotational friction of the components relative to one another.

The stem feature (104) further extends into the distal end of the housing component (112), which includes an additional axial bore section within which a distal sleeve (114) is located. As with the proximal sleeve (108), the distal sleeve (114) utilizes UHMWPE as a friction-reducing and biocompatible bearing for rotation of the stem (104) relative the housing (110). The distal end of the stem feature (104) is drilled and tapped to accept a threaded fastener (118). The threaded fastener in this embodiment is a hex fastener (118), which allows for easier manufacturability due to the positive engagement of hex wrench tools, but may be any fastener known in the art. The use of a thread locking material ensures positive retention of the fastener (118) when affixed within a patient.

Figure 2:
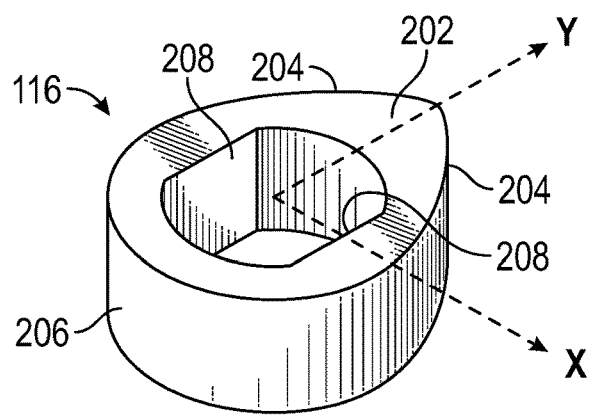
FIG. 2 is a close-up perspective view of the lobe ring utilized in the rotational device embodiment.

The fastener (118) also retains a lobe ring (116) on the end of the stem (104). The lobe ring (116) fits within a mating groove feature (120) within the distal end of the housing (112), and is designed to provide a positive and gradual stop to rotation of the stem (104) to prevent over-rotation. FIG. 2 is a close-up perspective view of the lobe ring (116) in the present embodiment, showing the features that prevent this over-rotation. As shown, the lobe bottom (206) is essentially circular, with the lobe top (202) extended in the "Y" direction. Within the mating groove (120) the lobe top (202) positively engages the mating groove (120) at each extreme of rotation, preventing further rotation (or "over-rotation"). Gradual ramps (204) are included to ease the transition to the lobe top (202), which slow the rotation within the groove (120), thereby preventing "hammering" impulse of the rotational device during rapid and full rotation of the prosthesis by the patient. Positive locating flats (208) in the bore of the lobe (116) mate with flats (106) on the stem feature (104) to prevent rotation of the lobe (116) with respect to the stem (104). Another embodiment might utilize a lobe ring with a simple tab feature and no ramps, but hammering of the rotational device might result.

In another embodiment the lobe ring (116) does not utilize a physical rotation stop. Inside the patient, this embodiment allows the stem (104) to rotate to the fullest extent allowed by the patient's soft tissue. This can be advantageous because it prevents the harsh rotational stop "hammering" impulses that might be perceived by the patient as with the previous embodiment. The stops may be removed from within the groove (120), or the ramps may be removed from the lobe ring, making the lobe ring more circular in shape.

The machined axial component, the housing component, and all other metal components of the embodiment are manufactured from biologically compatible and stable metals. In the instant embodiment the axial and housing components are titanium, but may be surgical stainless steel, niobium, gold, platinum, or the like. Moreover, combinations of metals and/or biocompatible polymers may also be utilized and are within the scope of the claimed invention. Internal components, likewise, are manufactured from these same metals and/or polymers. For example, the lobe ring component (116) of the present embodiment is manufactured from UHMWPE to reduce impulse forces that can result from rapid rotation of the device to a limit. However, metals may also be utilized to improve the wear resistance of the device. In another embodiment, the device comprises a combination of metal and polymer coating on the outer wear surface to soften the impulse. Yet another embodiment may utilize a polymer body with a metal layer on the outer wear surface to improve the wear characteristics while providing a reduction in impulse.

Figure 3:
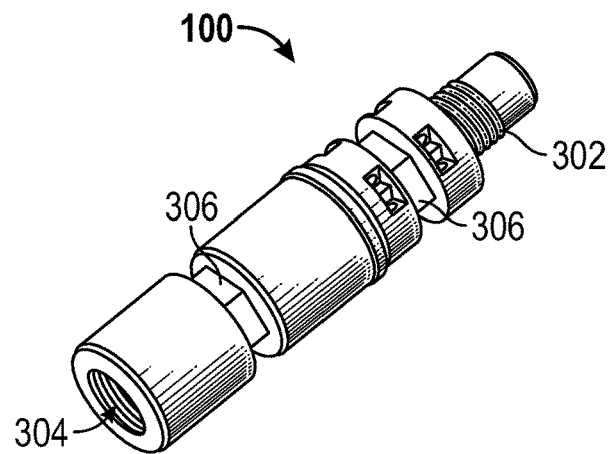
FIG. 3 is an assembled perspective view of the rotational device embodiment.

FIG. 3 is an assembled perspective view of the embodiment showing the modular rotational device (100) in its assembled form, as it would be utilized to complete a torsionally stabilized humeral or femoral prosthesis. A male threaded coupler (302) and a female threaded coupler (304) feature allow for the attachment of additional endoprosthetic devices. For example, modular spacers, intramedullary stems, and joint components necessary to construct a complete endoprosthetic may be attached. Further, other embodiments of the modular rotational device (100) might feature only male threaded couplers or female threaded couplers, or might have the two reversed from that of the present embodiment. Hexagonal features (306) are provided to allow the use of an open-end wrench when assembling other prosthesis devices to the embodiment.

The modular rotational device in other embodiments may include combined joint features. For example, FIG. 4 presents an exploded perspective view of an embodiment of a modular distal humeral prosthesis device incorporating an embodiment of the rotational device. The machined axial component (402) is visible, along with the stem feature (404) and proximal sleeve (408) as in the previous embodiment. However, in this embodiment the distal humeral component housing (410) provides the through-hole axial bore that accepts the proximal sleeve (408) and stem (404). A distal sleeve (412) is located within a housing groove, as is a lobe ring (414). A fastener (418) and washer (416) retain the lobe ring on the stem (404), with flats (406) on the stem positively locating the lobe ring (416) within the housing groove (420). Completing the distal humeral component (400) are axle sleeves (422) for supporting a joint axle (424) within the housing distal end. The axle sleeves (422), as with the proximal and distal sleeves (408 and 412), are UHMWPE construction to reduce friction during rotation. FIG. 5 is an assembled perspective view of this embodiment.

Figure 6:
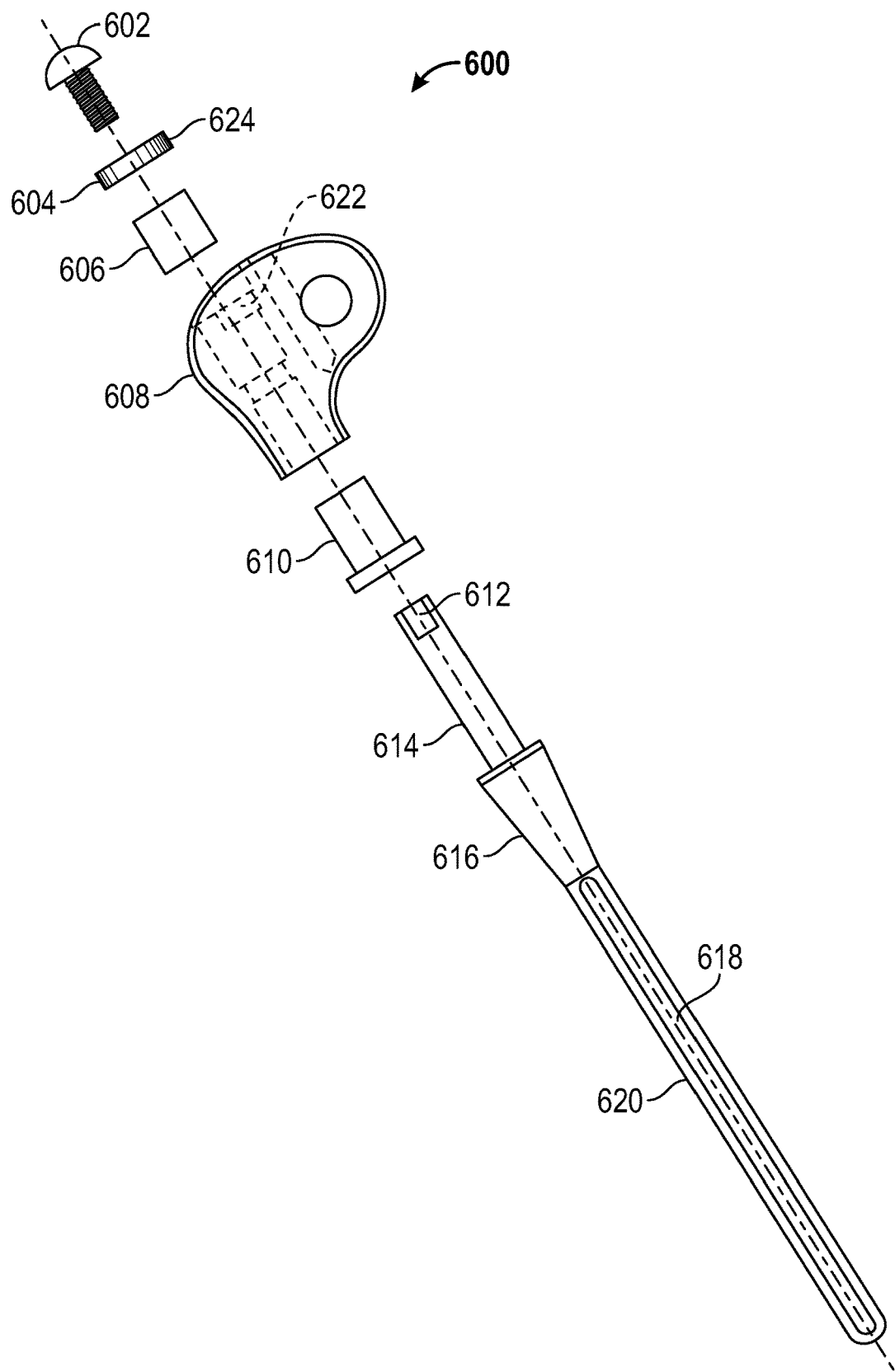
FIG. 6 is an exploded view of a forearm device for completion of a humeroulnar/humeroradial articulation with the disclosed embodiment.

To complete the construction of a humeral prosthesis with a humeroulnar articulation, it is helpful to describe the device that, when combined with the previous embodiment, may form the humeroulnar articulation. FIG. 6 is an exploded view of a forearm device for completion of a humeroulnar/humeroradial articulation with the disclosed invention. As shown, an intramedullary ulnar stem (620) features longitudinal grooves (618) extending from the distal end to the proximal end of the stem for rotational stability when cemented into the patient's ulna or radius. Also featured is a taper segment (616) that is also coated with a means for apposition of bone (i.e., texture or chemical treatment). The proximal end of the ulnar stem (620) includes a shaft segment (614) that fits within and passes through a first thrust sleeve (610) and a second bearing sleeve (606), and ultimately engages within the positive engagement flats (208) of a lobe ring (604) similar to that depicted in FIG. 2. A lobe ring fastener (602) engages the ulnar stem shaft (614) and retains the assembly. The sleeves (610 and 606) fit within machined recesses within the elbow assembly (600) body. The first thrust sleeve (610) features a thrust surface that minimizes friction between the ulnar stem taper (616) and the elbow assembly body (608). The thrust surface is comprised of the same plastic as the sleeve (610). However, the thrust surface may also be comprised of a suitable medical grade metal or polymer different from that of the sleeve.

To afford rotation and to minimize friction while doing so, the ulnar stem shaft (614) utilizes similar materials as the articulating surfaces. For example, the shaft may be coated with cobalt chrome, pyrocarbon, ceramic, or other medical-grade, corrosion inhibiting, friction-reducing material. Likewise, the plastic sleeves (610 and 606) may utilize a medical-grade polymer, including UHMWPE, to reduce friction.

The lobe ring (604) in this embodiment is similar in form and function to the previously discussed lobe ring. As shown, a positive engagement feature is provided that mates (or interlocks) with a related feature (612) on the ulnar stem shaft (614), causing the lobe ring and ulnar stem to rotate in unison. A tab feature (624) on the outer radius of the lobe ring (604) moves within a rotational groove feature (622) in the body (608) and serves to limit the degree of rotation within the elbow assembly body (608). In this embodiment the groove (622) is machined within the elbow assembly body (608) and is sized to allow the ulnar stem (620) to rotate approximately 180 degrees to approximate the normal range of rotational motion of a patient's wrist and hand, with the tab feature (624) contacting the ends of the groove feature (622) as in previous embodiments. The overall range of motion may be adjusted by changing the overall length of the rotational groove (622) to either increase or decrease this range (i.e., greater than or less than 180 degrees). Further, in another embodiment, the lobe ring is a machined feature of the ulnar stem shaft (420).

Figure 7:
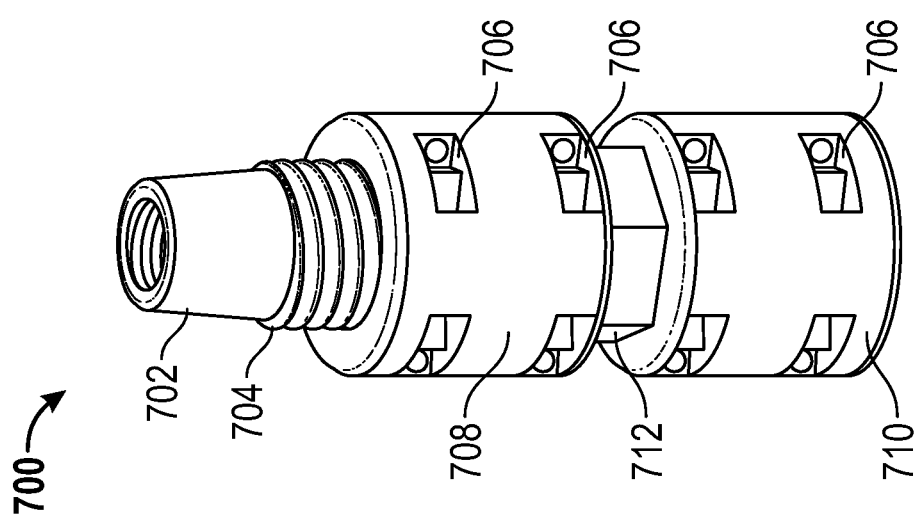
FIG. 7 is an embodiment of a modular spacer for use with the modular humeral prosthesis as disclosed herein.

FIG. 7 is an embodiment of a modular spacer for use with the modular humeral prosthesis as disclosed herein. The overall length of the spacer (700) allows the surgeon to size the resulting humeral prosthesis to fit the patient's anatomy. For example, a surgery center might maintain modular spacers in various lengths—10 mm to 50 mm—that afford the ability to tailor the length of the repair in 10 mm increments to fit the patient.

The proximal end of the spacer features a Morse taper (702) followed by threads (704) for engaging a mating female end on another spacer. The Morse taper is a common machined taper that is used to positively join machined components. The proximal end (708) of the body of the spacer includes holes (706) for suture attachment of soft tissue. As with the modular rotational device embodiments, the body includes a hex feature (712) for engagement by an open-ended wrench of appropriate size, which is used during assembly of the modular devices. The distal end (710) features a complementary female threaded coupler (not visible) for engaging with the male threaded coupler (see 702/704) of another spacer or rotational device.

Figure 8:
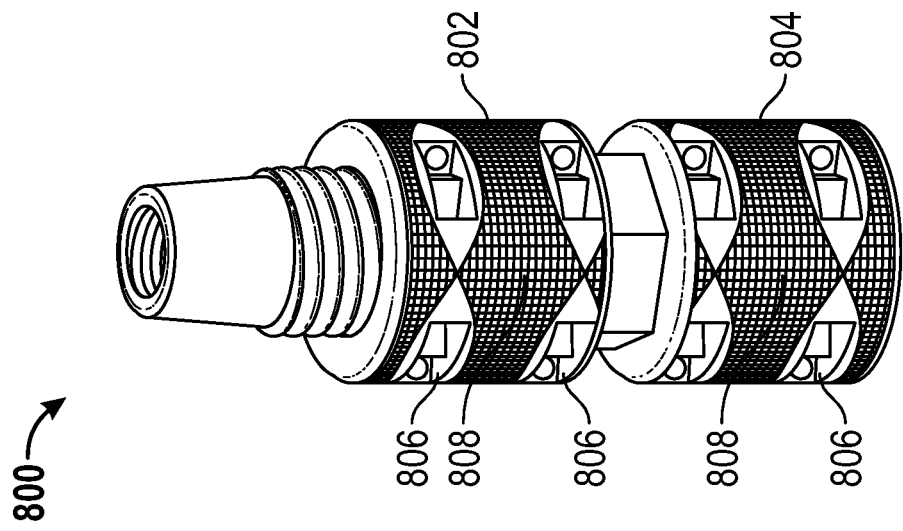
FIG. 8 is an embodiment of the modular spacer with surface treatment for soft tissue attachment.
Figure 9:
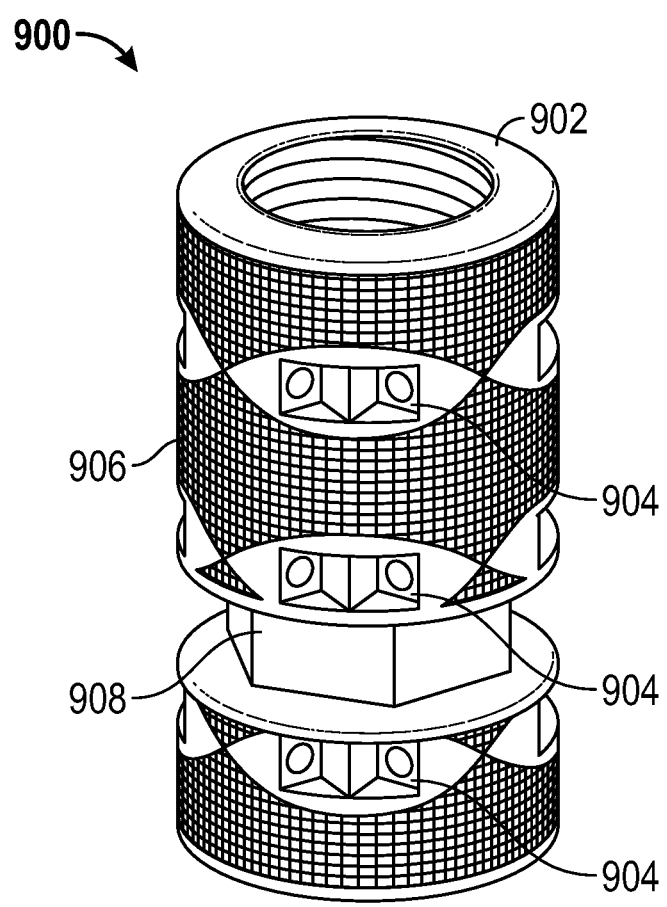
FIG. 9 is another embodiment of the modular spacer with surface treatment for soft tissue attachment.

FIG. 8 is an embodiment of the modular spacer with surface treatment for soft tissue attachment. The proximal (802) and distal (804) body segments provide through-hole suture attachment features (806) and also includes a porous mesh surface treatment (808). FIG. 9 presents yet another embodiment of the modular spacer with surface treatment for soft tissue attachment. In this embodiment the spacer provides only female thread couplers (902) for attachment. Visible once more are the suture attachment through holes (904) and surface texture (906), and hex wrench feature (908). The porous mesh surface treatment creates a three-dimensional surface structure that is similar to cancellous bone, and which encourages the attachment of soft tissue. The porous mesh surface treatment is created using the known process for creating common trabecular metal, albeit with a greater porosity. For example, the surface texture may be created by thermal deposition in which the texture is effectively "printed" onto the surface atom-by-atom. Biocompatible materials, including tantalum, may be utilized in this process to create the three-dimensional surface texture structure. In the instant invention, it has been shown that a surface texture porosity of approximately 600 to 800 microns encourages soft tissue attachment to treated implants. Suturing the soft tissue to the suture attachment features (906) allows the soft tissue to affix to the surface structure (906) as the patient heals.

A successful limb-sparing procedure for oncological purposes can be divided into three stages. The first stage involves tumor resection, and must spare significant tissue structures to support reconstruction while obtaining adequate oncologic margin to eliminate diseased tissue. The second stage involves the affixation of a stable, painless skeletal reconstruction (typically an endoprosthetic device). Third, the surrounding and supporting soft tissue is required to restore functionality to the skeletal reconstruction. The performance of the first two steps of this procedure is well understood, so it is not necessary to provide such detail herein. However, the endoprosthetic device and its use disclosed herein have heretofore never been contemplated.

Figure 10:
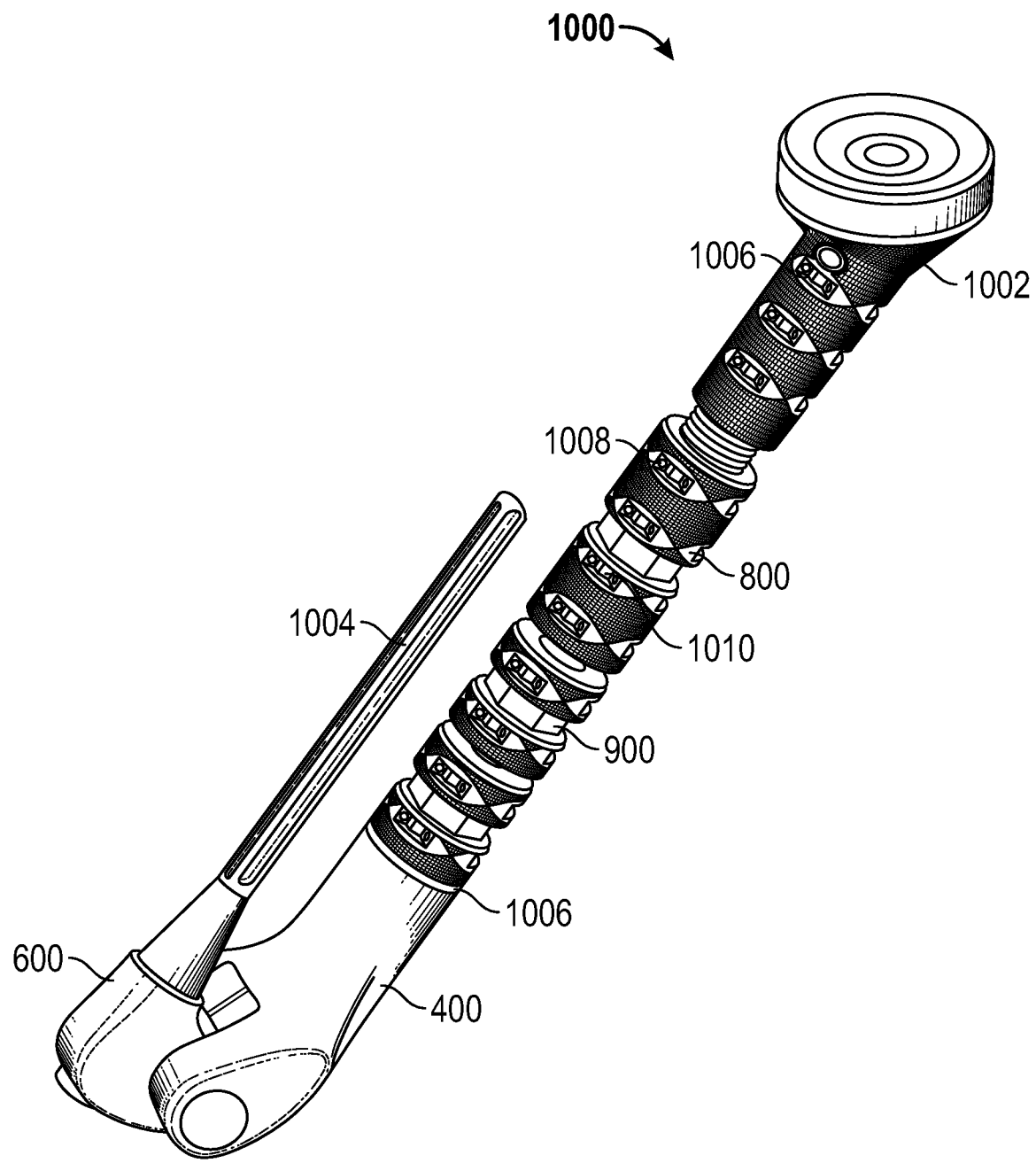
FIG. 10 is an embodiment of a complete modular humeral prosthesis with rotational device, and featuring a reverse shoulder upper extremity and humeroulnar/humeroradial articulation.

FIG. 10 presents an embodiment of a complete modular humeral prosthesis with rotational device, and featuring a reverse shoulder upper extremity and humeroulnar/humeroradial articulation (1000). The metaphyseal segment (1002) in this embodiment provides a spherical insert for engagement with a metal ball fixated within the glenoid cavity of the patient. The shaft is comprised of any number and size of modular spacers (800, 900) necessary to achieve the correct length for the repair. The lower extremity (400) features a rotational device (1006) as previously described, as well as a forearm device (600) to form the humeroulnar articulation. The intramedullary stem (1004) is affixed within an axial borehole in the ulna or radius of the patient. Normally during surgery the intramedullary stem (1004) is affixed to the patient's ulna. Following resection of the appropriate length of the ulna, the medullary canal is reamed to receive the stem (1004) to a depth up to the stem taper and is packed with cement. If the prosthetic device is being fixated in the patient's right arm, the stem (1004) is rotated counterclockwise as viewed from the distal end to the stop of its rotation and, with the patient's palm facing skyward, the stem is inserted into the medullary canal. The longitudinal channels of the ulnar stem in conjunction with the cement provide rotational stability within the ulna. If the patient's ulna is not serviceable, then the device may also be affixed to the patient's radius in the same fashion.

To complete the procedure (third stage) it is necessary to reattach the surrounding and supporting soft tissue to the prosthesis. The present embodiment provides a porous mesh surface treatment and strategic suture attachments to effect reattachment. For example, the subscapularis must be reattached to the area of the prosthetic device that represents the lesser tuberosity of the original humerus (1006). The subscapularis tendon is affixed to a suture attachment feature in this area (1006) and, over time, the tendon collagen fibers anchor the tendon into the porous mesh surface treatment present at this enthesis. Likewise, the pectoralis major must be reattached to the area of the prosthetic device that represents the lateral lip of intertubercular groove of original humerus (1008). Accordingly, the pectoralis major tendon is affixed to a suture attachment feature in this area (1008) and, over time, this tendon collagen fibers anchor the tendon into the porous mesh surface treatment present at this enthesis. This is repeated for the remaining muscles, including the rotator cuff muscles, triceps, brachialis, and brachioradialis (1010).

Figure 11:
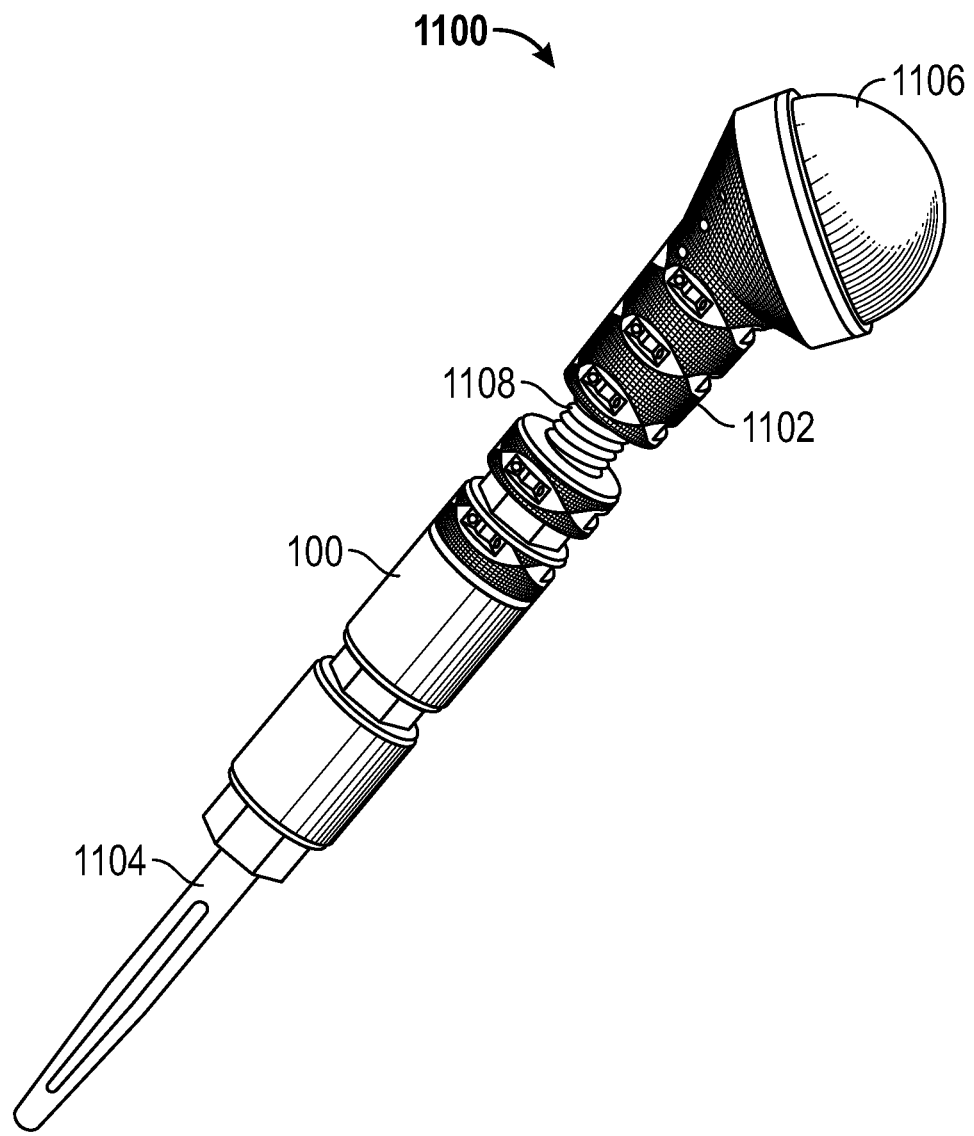
FIG. 11 is an embodiment of a partial modular humeral prosthesis with rotational device, and featuring a normal shoulder upper extremity.

FIG. 11 is an embodiment of a partial modular humeral prosthesis with rotational device, and featuring a normal shoulder upper extremity. This configuration may be used in instances in which resection of a diseased proximal portion of a humor leaves sufficient shaft length for insertion and affixation of an intramedullary stem (1104) through common means. The metaphyseal segment (1102) includes a ball component (1106) for engagement with the glenoid process of the patient, or with a glenoid prosthetic device. A rotational device (100) as described herein is also included, with the rotational aspect nearest to the stem (1104). It is possible to add additional modular spacers (1108) to establish the proper length of the repair to ensure symmetry with regard to the patient's arms.

Figure 12:
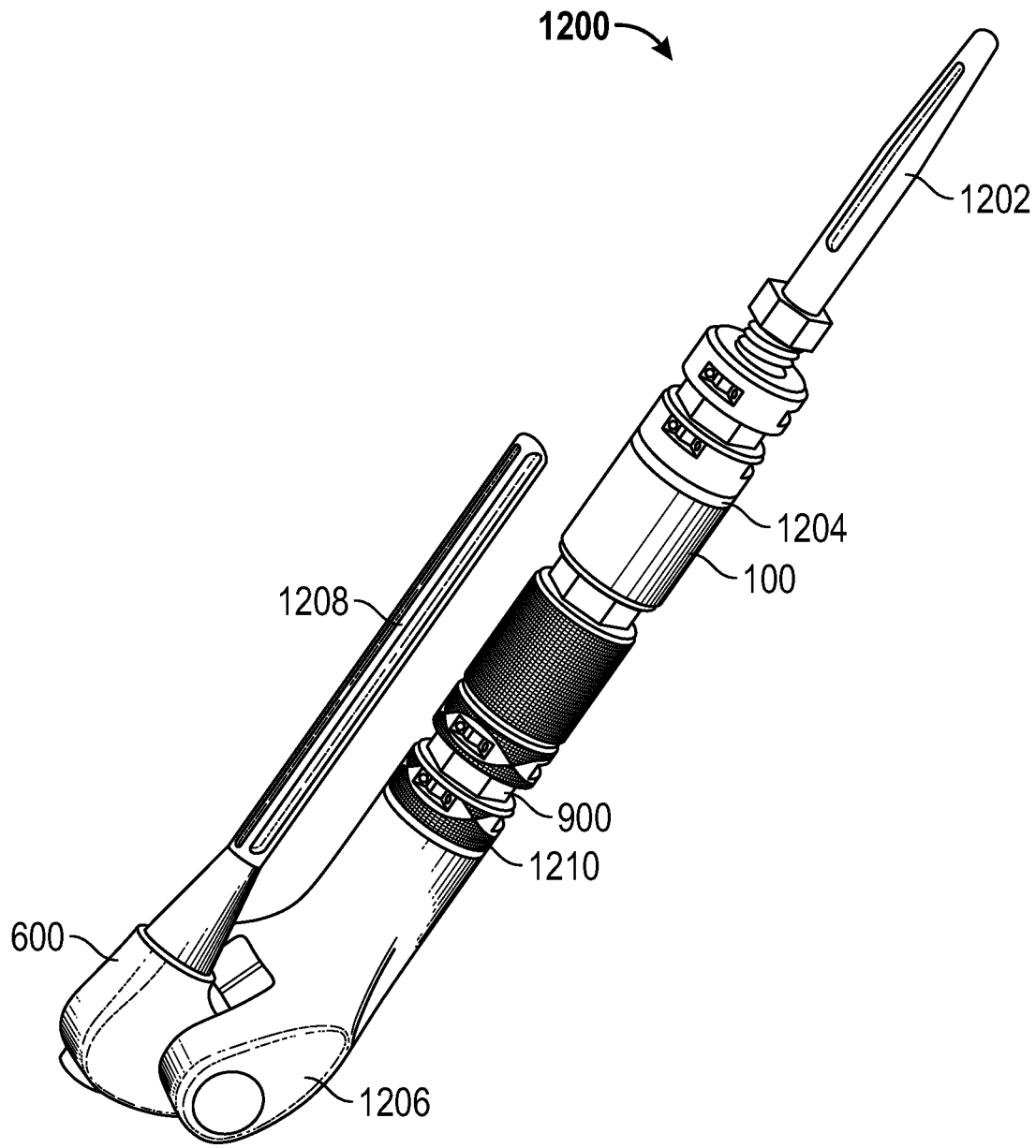
FIG. 12 is an embodiment of a partial modular humeral prosthesis with rotational device, and featuring a humeroulnar/humeroradial articulation.

FIG. 12 is an embodiment of a partial modular humeral prosthesis with rotational device, and featuring a humeroulnar/humeroradial articulation. This endoprosthetic device configuration (1200) may be used in instances in which the humeroulnar/humeroradial articulation must be resected due to disease, yet the glenohumeral articulation is retained. As shown, a proximal intramedullary stem (1202) is affixed within the patient's remaining humerus shaft segment, and a radial intramedullary stem (1208) is affixed within the patient's remaining radius shaft segment. A modular rotational device (100) is included, with the rotational device (1204) nearest the humeral stem (1202). A modular spacer (900) is incorporated as necessary to establish the proper repair length to ensure symmetry of the patient's arm length. The modular spacer (900) includes porous mesh metal surface treatment to ensure affixation of the soft muscle tissue of the forearm.

The rotational device embodiment may also be utilized with femoral prosthetic devices to, likewise, prevent excessive torsional stresses during rapid full rotation of the patient's lower leg with respect to the hip. These torsional stresses can weaken the stem fixation site, and can cause dislocation of the acetabulofemoral articulation (hip socket) due to the impulse felt at the acetabulofemoral articulation at full rotation. As with the humeral prosthetic device, the rotational device is positioned proximate the intramedullary stem. Such a configuration is depicted in FIG. 13.

Figure 13:
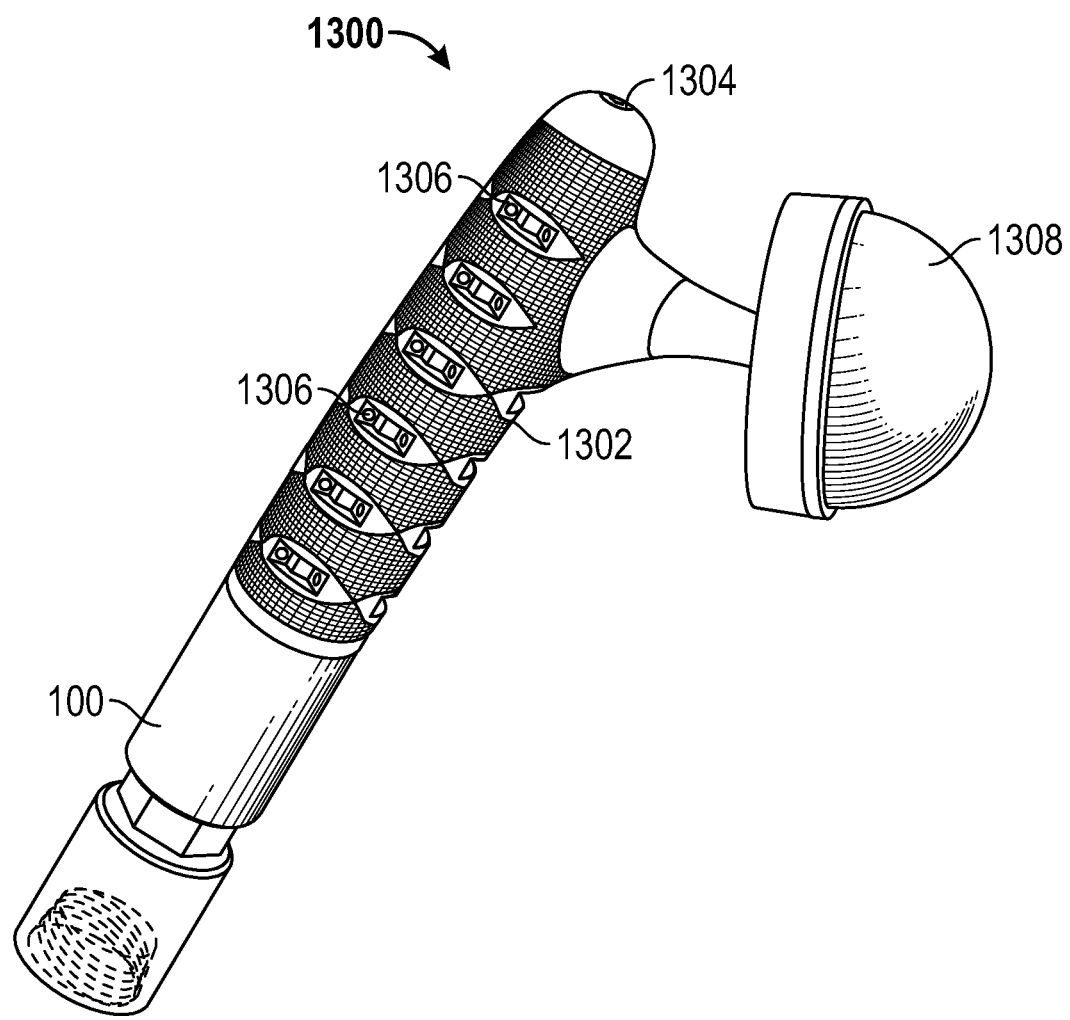
FIG. 13 is an embodiment of a partial modular femoral prosthesis with rotational device, and featuring a normal femoral head.

FIG. 13 is an embodiment of a partial modular femoral prosthesis with rotational device, and featuring a normal femoral head. This endoprosthetic device configuration (1300) utilizes the modular rotational device (100) as described herein, coupled with the trochanter segment (1302) featuring a ball component (1308) for engagement with the acetabulum. The modular rotational device (100) is positively retained by the trochanter segment (1302) through use of a hex-headed locking screw (1304) that runs the length of the trochanter segment (1302). As depicted, the outer surface of the proximal segment (1302) includes a porous mesh surface treatment as previously described, to effect soft tissue attachment to the prosthesis. Suture attachment features (1306) provide for positive retention of the soft tissue until healing and attachment occurs.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are intended therein. Further, the recitation of method steps does not denote a particular sequence for execution of the steps. Such method steps may therefore be performed in a sequence other than that recited unless the particular claim expressly states otherwise.

I claim:

1. A modular rotational device for torsionally stabilizing an endoprosthesis bone segment located wholly internal to a patient, the device comprising:
  a first threaded coupler including an elongated stem extending therefrom;
  a housing having a proximal end and a distal end with an axial bore therethrough;
  a proximal sleeve positioned within the housing proximal end axial bore, the proximal sleeve having an axial bore therethrough for receiving the elongated stem, the proximal sleeve reducing the rotational friction of the elongated stem with respect to the housing proximal end;
  a distal sleeve positioned within the housing distal end axial bore, the distal sleeve having an axial bore therethrough for receiving the elongated stem; the distal sleeve reducing the rotational friction of the elongated stem with respect to the housing distal end;
  a distal fastener for positively engaging the elongated stem within a distal end cavity to retain the stem within the housing distal end; and
  a second threaded coupler on the distal housing end, the first threaded coupler and the second threaded coupler each accepting an additional complementary threaded endoprosthesis device attached thereto, the first threaded coupler rotatable with respect to the second threaded coupler post-fixation within a patient.

2. The device of claim 1, the device further comprising:
  a lobe ring affixed to the elongated stem for limiting the degree of the rotation of the elongated stem within the housing.

3. The device of claim 1, the device further comprising:
  a lobe ring affixed to the elongated stem, the lobe ring including a ramp feature for gradually arresting the relative joint rotation.

4. The device of claim 1, the device further comprising:
  a lobe ring affixed to the elongated stem and a rotational stop within a distal end cavity for engaging a feature on the lobe ring for limiting the degree of the rotation of the elongated stem within the housing.

5. The device of claim 1, the device further comprising:
  a distal end cavity including threads for attachment of an endoprosthesis component thereto.

6. The device of claim 1, the device further comprising:
  at least one Morse taper for affixation of an endoprosthesis component thereto.

7. The device of claim 1, the device further comprising:
  a porous mesh metal surface treatment for soft tissue growth attachment thereto.

8. The device of claim 1, the housing further comprising:
  a porous mesh surface treatment including a plurality of through hole suture attachments for suture attachment of soft tissue thereto.

9. The device of claim 1, the device further comprising:
  at least one hex feature for engagement of a gripping tool therewith.

10. The device of claim 1, the device further comprising:
a hex feature separating the housing proximal end from the housing distal end, the hex member for engagement of a gripping tool therewith.

11. A modular rotational device for torsionally stabilizing an endoprosthesis bone segment located wholly internal to a patient, the device comprising:
a first threaded coupler including an elongated stem extending therefrom;
a housing having a proximal end and a distal end with an axial bore therethrough for receiving the elongated stem; and
the housing distal end including a second threaded coupler, both the first threaded coupler and the second threaded coupler each accepting an additional complementary threaded endoprosthesis device attached thereto, the first threaded coupler rotatable with respect to the second threaded coupler post-fixation within a patient.

12. The device of claim 11, the device further comprising:
a proximal sleeve positioned within the housing proximal end axial bore, the proximal sleeve having an axial bore therethrough for receiving the elongated stem, the proximal sleeve reducing the rotational friction of the elongated stem with respect to the housing proximal end.

13. The device of claim 11, the device further comprising:
a distal sleeve positioned within the housing distal end axial bore, the distal sleeve having an axial bore therethrough for receiving the elongated stem; the distal sleeve reducing the rotational friction of the elongated stem with respect to the housing distal end; and
a distal fastener for positively engaging the elongated stem within a distal end cavity to retain the stem within the housing distal end.

14. The device of claim 11, the device further comprising:
a lobe ring affixed to the elongated stem within the housing distal end for limiting the degree of the rotation.

15. The device of claim 11, the device further comprising:
a distal end cavity including threads for attachment of an endoprosthesis component thereto.

16. The device of claim 11, the device further comprising:
at least one Morse taper for affixation of an endoprosthesis component thereto.

17. The device of claim 11, the device further comprising:
a porous mesh metal surface treatment for soft tissue growth attachment thereto.

18. The device of claim 11, the housing further comprising:
a porous mesh surface treatment including a plurality of through hole suture attachments for suture attachment of soft tissue thereto.

19. The device of claim 11, the housing further comprising:
at least one hex feature for engagement of a gripping tool therewith.

20. The device of claim 11, the housing further comprising:
a hex feature separating the housing proximal end from the housing distal end, the hex member for engagement of a gripping tool therewith.

* * * * *